United States Patent
Jing (10) Patent No.: US 9,931,675 B2
(45) Date of Patent: Apr. 3, 2018

(54) SUBSTRATE MARK DETECTION APPARATUS AND SUBSTRATE MARK DETECTION METHOD

(71) Applicants: BOE Technology Group Co., Ltd., Beijing (CN); Hefei BOE Optoelectronics Technology Co., Ltd., Hefei (CN)

(72) Inventor: Yangkun Jing, Beijing (CN)

(73) Assignees: BOE Technology Group Co., Ltd., Beijing (CN); Hefei BOE Optoelectronics Technology Co., Ltd., Hefei (CN)

(*) Notice: Subject to any disclaimer, the term of this patent is extended or adjusted under 35 U.S.C. 154(b) by 118 days.

(21) Appl. No.: 15/170,493

(22) Filed: Jun. 1, 2016

(65) Prior Publication Data

US 2016/0354808 A1 Dec. 8, 2016

(30) Foreign Application Priority Data

Jun. 3, 2015 (CN) .......................... 2015 1 0299662

(51) Int. Cl.
*G01N 21/88* (2006.01)
*B07C 5/342* (2006.01)
*G01N 21/958* (2006.01)
*G01N 21/896* (2006.01)

(52) U.S. Cl.
CPC .......... *B07C 5/342* (2013.01); *G01N 21/8851* (2013.01); *G01N 21/958* (2013.01); *G01N 2021/888* (2013.01); *G01N 2021/8967* (2013.01)

(58) Field of Classification Search
CPC ................. B07C 5/3412; B07C 5/342; B07C 2501/0072; G01N 21/8851; G01N 21/8883; G01N 21/896; G01N 21/958; G01N 2021/888; G01B 11/22
See application file for complete search history.

(56) References Cited

U.S. PATENT DOCUMENTS

| | | | | |
|---|---|---|---|---|
| 5,680,215 A * | 10/1997 | Huber | ................. | G01B 11/306 356/237.1 |
| 8,286,780 B2 * | 10/2012 | Malek | ................. | B07C 5/3404 198/403 |
| 8,900,777 B2 * | 12/2014 | Chu | ................. | G03F 1/72 430/30 |
| 9,575,010 B2 * | 2/2017 | Ogawa | ............... | G01N 21/8851 |

(Continued)

*Primary Examiner* — Joseph C Rodriguez
(74) *Attorney, Agent, or Firm* — Banner & Witcoff, Ltd.

(57) ABSTRACT

A substrate mark detection apparatus includes: a detecting module, configured to detect a depth at which a mark is embedded in a substrate to be detected and determine whether the substrate is valid or not according to the depth at which the mark is embedded in the substrate; an information extracting module, configured to parse the mark to obtain parsed information in a case where the substrate is valid, query pre-stored information corresponding to the mark, determine whether the parsed information conforms to the pre-stored information or not, and if yes, to extract the pre-stored information and output the pre-stored information; a sorting module, configured to remove the substrate in a case where the substrate is invalid or the parsed information does not conform to the pre-stored information.

20 Claims, 6 Drawing Sheets

(56) References Cited

U.S. PATENT DOCUMENTS

| | | | |
|---|---|---|---|
| 2005/0073748 A1* | 4/2005 | Hayashi | B41M 5/262 359/566 |
| 2010/0162865 A1* | 7/2010 | Innocenzo | B26D 5/32 83/73 |
| 2010/0245792 A1* | 9/2010 | Bijnen | G03B 27/42 355/53 |
| 2011/0083791 A1* | 4/2011 | Nakazono | G01N 21/8914 156/64 |
| 2012/0114921 A1* | 5/2012 | Tsuda | B23K 26/0846 428/210 |
| 2016/0207822 A1* | 7/2016 | Ohigashi | C03B 33/037 |

* cited by examiner

SUBSTRATE MARK DETECTION APPARATUS AND SUBSTRATE MARK DETECTION METHOD

This application claims priority to and the benefit of Chinese Patent Application No. 201510299662.8 filed on Jun. 3, 2015, which application is incorporated herein in its entirety.

TECHNICAL FIELD

Embodiments of the present disclosure relate to a substrate mark detection apparatus and a substrate mark detection method.

BACKGROUND

Typically, when a glass substrate is in manufacture, marks will be formed on the substrate, and the marks can be used for confirming an ID of the substrate and can also be used for aligning; usually, these marks are higher than the surface of the substrate; when a rubbing alignment process is performed on the substrate, due to influence of the height of the marks, damage may be caused to a rubbing cloth, for example, the hairiness of the rubbing cloth, which is apt to cause undesirable linear rubbing defect, and generate relative undesirable alignment defects such as rubbing mura.

SUMMARY

At least one embodiment of the present disclosure provides a substrate mark detection apparatus and a substrate mark detection method, so as to accurately detect the mark formed inside the substrate.

An embodiment of the present disclosure provides a substrate mark detection apparatus, comprising: a detecting module, configured to detect a depth at which a mark is embedded in a substrate to be detected, and determine whether the substrate is valid or not according to the depth at which the mark is embedded in the substrate; an information extracting module, configured to parse the mark to obtain parsed information in a case where the substrate is valid, query pre-stored information corresponding to the mark, determine whether the parsed information conforms to the pre-stored information or not, and if yes, to extract the pre-stored information and output the pre-stored information; a sorting module, configured to remove the substrate, in a case where the substrate is invalid or the parsed information does not conform to the pre-stored information.

Another embodiment of the present disclosure provides a substrate mark detection apparatus, comprising: a processor; a memory; and one or more modules stored in the memory and configured for execution by the processor, the one or more module comprising instructions for: detecting a depth at which a mark is embedded in a substrate to be detected, and determining whether the substrate is valid or not according to the depth at which the mark is embedded in the substrate; parsing the mark to obtain parsed information in a case where the substrate is valid, querying pre-stored information corresponding to the mark, determining whether the parsed information conforms to the pre-stored information or not, and if yes, to extract the pre-stored information and output the pre-stored information; removing the substrate, in a case where the substrate is invalid or the parsed information does not conform to the pre-stored information.

Still another embodiment of the present disclosure provides a substrate mark detection method, comprising: detecting a depth at which a mark is embedded in a substrate to be detected, and determining whether the substrate is valid or not according to the depth at which the mark is embedded in the substrate; parsing the mark to obtain parsed information in a case where the substrate is valid, querying pre-stored information corresponding to the mark, determining whether the parsed information conforms to the pre-stored information or not, and if yes, to extract the pre-stored information and output the pre-stored information; removing the substrate, in a case where the substrate is invalid or the parsed information does not conform to the pre-stored information.

BRIEF DESCRIPTION OF THE DRAWINGS

In order to clearly illustrate the technical solution of the embodiments of the present disclosure, the drawings of the embodiments will be briefly described in the following; it is obvious that the described drawings are only related to some embodiments of the present disclosure and thus are not limitative of the present disclosure.

DETAILED DESCRIPTION

In order to make objects, technical details and advantages of the embodiments of the present disclosure apparent, the technical solutions of the embodiments will be described in a clearly and fully understandable way in connection with the drawings related to the embodiments of the present disclosure. Apparently, the described embodiments are just a part but not all of the embodiments of the present disclosure. Based on the described embodiments herein, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present invention belongs. The terms "first," "second," etc., which are used in the description and the claims of the present application for invention, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the components or the objects stated before these terms encompass the components or the objects and equivalents thereof listed after these terms, but do not preclude the other components or objects. The phrases "connect", "connected", etc., are not intended to define a physical connection or mechanical connection, but can include an electrical connection, directly or indirectly. "On," "under," "right," "left" and the like are only used to indicate relative position relationship, and when the position of the object which is described is changed, the relative position relationship can be changed accordingly.

Usually, in order to resolve a problem of influence of the height of a mark, a method of forming the mark inside a substrate is used; however, the method causes great difficulty in detecting the mark. At least one embodiment of the present disclosure provides a substrate mark detection apparatus and a substrate mark detection method for accurately detecting the mark formed inside a substrate.

Figure 1:
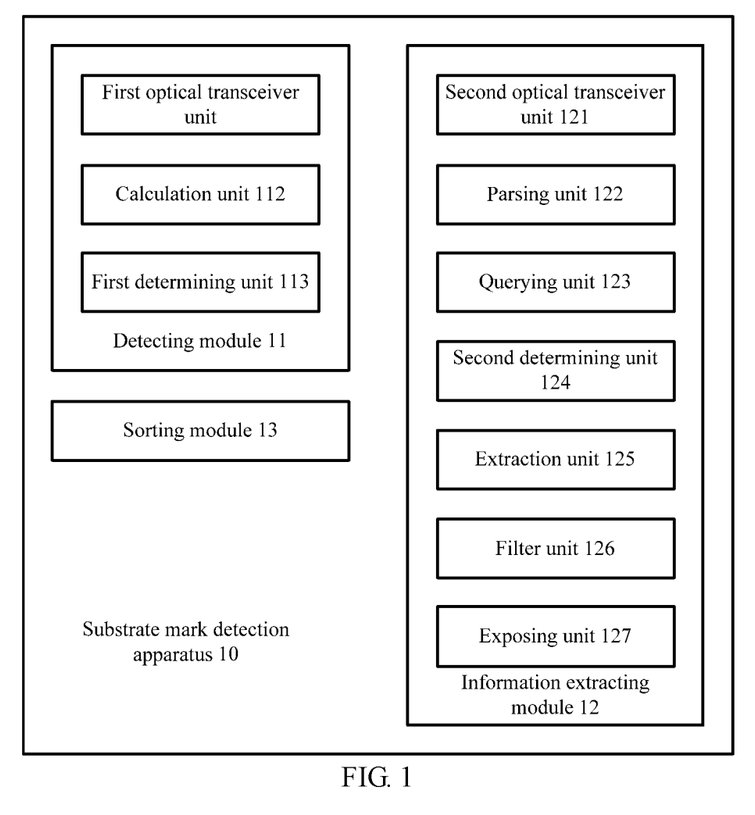
FIG. 1 shows a schematic block diagram of a substrate mark detection apparatus according to an embodiment of the present disclosure.

As illustrated in FIG. 1, a substrate mark detection apparatus 10 according to an embodiment of the present disclosure comprising: a detecting module 11, configured to detect a depth at which a mark is embedded in a substrate to be detected and determine whether the substrate is valid or not according to the depth at which the mark is embedded in the substrate; an information extracting module 12, configured to parse the mark to obtain parsed information in a case where the substrate is valid, query pre-stored information corresponding to the mark, determine whether the parsed information conforms to the pre-stored information or not, and if yes, to extract and output the pre-stored information; and a sorting module 13, configured to remove the substrate, in a case where the substrate is invalid or the parsed information does not conform to the pre-stored information.

By detecting the mark in the substrate and determining according to the depth at which the mark is embedded in the substrate, the substrate mark detection apparatus according to the above-described embodiment of the present disclosure can conveniently and accurately determine the validity of the substrate, so as to avoid detection of an invalid substrate in a subsequent process, improve overall efficiency of detecting the substrate, and can also remove the substrate, for which parsed information does not conform to the pre-stored information, and therefore the substrate can be accurately aligned in a subsequent cell-assembly process.

In a process of embedding the mark inside the substrate, on one hand, the substrate may be marked as valid or not by setting the depth at which the mark is embedded in the substrate, for example, in a process before detecting the depth at which the mark is embedded, the substrate is detected to have a quality problem and should not enter the subsequent cell-assembly process, then the mark can be embedded in the substrate at such a certain depth that the detecting module 11 can detect that the substrate is an invalid substrate, to facilitate the sorting module 13 to remove the substrate.

On the other hand, information (for example, identity information and position information, etc.) of the substrate can be recorded by setting the content of the mark; for example, the substrate does not suffer a certain quality problem, then the detecting module 11 will not determine it to be invalid, but the position information in the parsed information obtained through the parsing process of the information extracting module 12 according to the mark in the substrate does not conform to the position information in the pre-stored information, this result indicates that the substrate does not have a position accurate enough, and the substrate cannot be accurately aligned and assembled in the subsequent cell-assembly process and thus is also removed by the sorting module 13.

By detecting the mark in the substrate and determining according to the depth at which the mark is embedded in the substrate, validity of the substrate can be conveniently and accurately determined, so that detecting for an invalid substrate in the subsequent process can be avoided and overall detecting efficiency of the substrate can be improved, and further the substrate whose parsed information does not conform to the pre-stored information can be removed, and the substrate entering the subsequent cell-assembly process can be accurately aligned and assembled.

In some examples, an exemplary detecting module 11 includes: a first optical transceiver unit 111, configured to emit a detection light ray to a position of a first surface of the substrate corresponding to the mark, and receive a first light ray reflected by the first surface and a second light ray reflected by an upper surface of the mark; a calculation unit 112, configured to calculate the depth at which the mark is embedded in the substrate, according to a first transmission distance of the first light ray and a second transmission distance of the second light ray; and a first determining unit 113, configured to determine whether a relationship between depths at which a plurality of marks are embedded in the substrate including the plurality of marks satisfies a preset relationship, to determine whether the substrate is valid or not. For example, if the relationship between the depths at which the plurality of marks are embedded in the substrate including the plurality of marks does not satisfy the preset relationship, then the substrate is determined to be invalid, or, for example, if the relationship between the depths at which the plurality of marks are embedded in the substrate including the plurality of marks satisfies the preset relationship, then the substrate is determined to be invalid.

The depth at which a mark is embedded in a substrate inside the substrate can be detected accurately and quickly by the way of light irradiation so as to accurately and quickly determine whether the substrate is valid or not.

Figure 2:
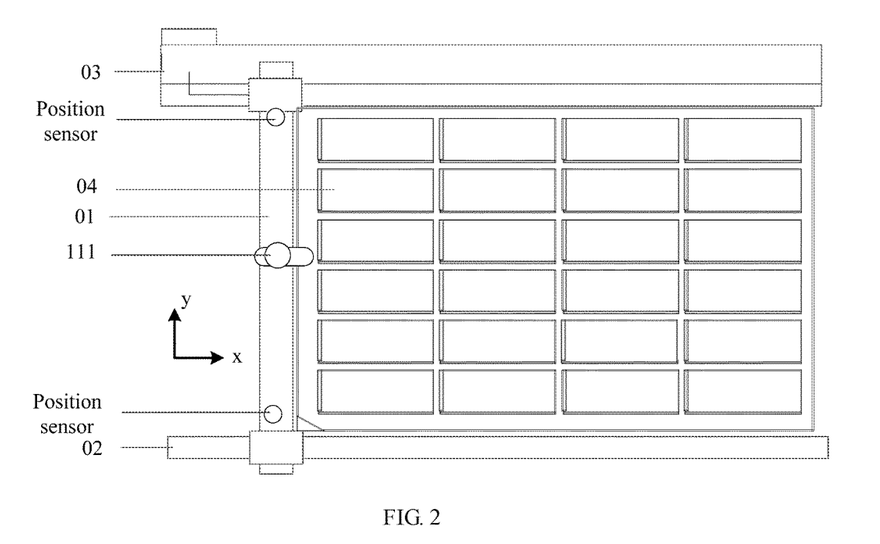
FIG. 2 shows a structural schematic diagram of a substrate mark detection apparatus according to another embodiment of the present disclosure.

For example, in a structure illustrated in FIG. 2, the first optical transceiver unit 111 may be an infrared detector, disposed on a horizontal beam 01, which can move along a y-axis on the horizontal beam 01 (the horizontal beam 01 including a y-direction guide rail), the guide rail 02 can drive the horizontal beam 01 to move along an x-axis as driven by an electrohydraulic servo cylinder 03 or the like, so that the infrared detector can be moved scan throughout the substrates 04.

For example, if the preset relationship is that the substrate is valid when a difference between the depths at which any two marks are embedded in the substrate among the plurality of marks is less than or equal to 0.1 mm, then in the detecting process, when it is detected in a preceding process in a production line that a substrate A has a defect and is an invalid substrate, marks a1 and a2 are embedded in the substrate A, a distance from the upper surface of the mark a1 to the upper surface of the substrate A is 0.5 mm, and a distance from the upper surface of the mark a2 to the upper surface of the substrate A is 0.3 mm, a difference between depths at which the two are embedded in the substrate A is 0.2 mm, then the first determining unit 113 can determine that the value of the difference 0.2 mm is greater than the preset value 0.1 mm, which means that the relationship between the marks does not conform to the preset relationship, and then the substrate is determined as being invalid.

For example, if the preset relationship is that the substrate is invalid when the difference between the depths at which any two marks are embedded in the substrate among the plurality of marks is greater than 0.1 mm, then in the detecting process, when it is detected in the preceding process in the production line that the substrate A has a defect and is an invalid substrate, marks a1 and a2 are embedded in the substrate A, a distance from the upper surface of the mark a1 to the upper surface of the substrate A is 0.5 mm, and a distance from the upper surface of the mark a2 to the upper surface of the substrate A is 0.3 mm, the difference between the depths at which the two marks are embedded in the substrate A is 0.2 mm, then the first determining unit 113 can determine that the value of the different 0.2 mm is greater than the preset valued 0.1 mm, which means that the relationship between the marks conforms to the preset relationship, and then the substrate is determined as being invalid.

In some examples, the detecting module 11 includes: a first optical transceiver unit 111, configured to emit a detection light ray to a position of a first surface of the substrate corresponding to the mark and receive a first light ray reflected by the first surface and a second light ray reflected by an upper surface of the mark; a calculation unit 112, configured to calculate the depth at which the mark is embedded in the substrate, according to a first transmission distance of the first light ray and a second transmission distance of the second light ray; and a first determining unit 113, configured to determine whether the depth at which the mark is embedded in the substrate is within a preset range of depth, if the depth at which the mark is embedded in the substrate is not within the preset range of depth, determine that the substrate is invalid, and if the depth at which the mark is embedded in the substrate is within the preset range of depth, determine that the substrate is valid.

In a case where the substrate includes a plurality of marks, the first determining unit 113 is further configured to determine whether a depth for which each mark is embedded in the substrate is within the preset range of depth or not, if the depth for which any mark is embedded in the substrate is not within the preset range of depth, determine that the substrate is invalid. If the depth for which each mark is embedded in the substrate is within the preset range of depth, then the substrate is determined to be valid.

For example, if the preset range of depth is from 0.2 mm to 0.4 mm, then in the detecting process, when it is detected in the preceding process in a production line that the substrate A has a defect and is an invalid substrate, marks a1 and a2 are embedded in the substrate A, a distance from the upper surface of the mark a1 to the upper surface of the substrate A is 0.5 mm, and a distance from the upper surface of the mark a2 to the upper surface of the substrate A is 0.3 mm, the first determining unit 113 can determine that the depth at which the mark a1 is embedded in the substrate A is not within the preset range of depth, and the substrate A is determined to be invalid.

It should be noted that, the preset relationship and the preset range of depth as described above can both be selected in a particular application. In addition, the above two modes of determining whether the substrate is invalid or not may be used separately, and on a basis that one determination condition has been established, another determination may be continued and conducted as well; for example, on a basis that it is determined that the difference between the depths at which any two marks are embedded in the substrate among the plurality of marks satisfies the preset relationship, it may be further determined whether the depth for which each mark is embedded in the substrate is within the preset range of depth or not, so as to further improve the accurate determination regarding whether the substrate is valid or not.

For example, the first determining unit 113 may further be configured to determine a shape of the upper surface of the mark according to the second transmission distance of the second light ray.

If it is determined that the upper surface of the mark is a plane, then it is determined that a plurality of sub-distances included in the second transmission distance are equal, and the calculation unit 112 calculates the depth at which the mark is embedded in the substrate according to any sub-distance in the second transmission distance and the first transmission distance.

If it is determined that the upper surface of the mark is not a plane, then it is determined that the plurality of sub-distances included in the second transmission distance are not equal to each other, and the calculation unit 112 may calculate the depth at which the mark is embedded in the substrate according to a maximum sub-distance in the second transmission distance and the first transmission distance.

Because the mark has a certain microscopic shape itself, the shape of its upper surface may be in a number of shapes such as a plane, an inclined plane, and a curved surface, the second light ray irradiated on the mark's upper surface and reflected therefrom also has a certain area, and the first determining unit 113 may, according to the information of the optical path difference in each region in the second light ray received, determine the shape of the upper surface of the mark. For example, if there is no optical path difference, then it can be determined that a reflecting surface is a plane, that is, the upper surface of the mark is of a plane; if there is an optical path difference and the optical path differences of continuously adjacent regions are identical, then it can be determined that the reflecting surface is an even inclined plane, that is, the upper surface of the mark is of an inclined plane; and if the optical path differences of the continuous adjacent regions changes from negative to positive, then the reflecting surface is a concave surface, i.e., the upper surface of the mark is of a concave surface.

For example, when the upper surface of the mark is of a curved surface, the second transmission distances of the second light rays reflected by different regions in the upper surface are different, and thus, the depths at which the different regions of the mark are embedded in the substrate and which is obtained through calculation are also different. The depth at which the mark is embedded in the substrate is calculated by uniformly selecting the maximum sub-distance in the second transmission distance and the first transmission distance, thereby standards for calculating the depths at which the plurality of marks are embedded are uniform when the upper surfaces of the plurality of marks are not planes, so as to improve accuracy of subsequent calculation.

For example, the information extracting module 12 includes: a second optical transceiver unit 121, configured to emit a light ray to irradiate the substrate determined to be valid by the detecting module, and obtain a bitmap image formed by a projection of the mark; a parsing unit 122, configured to parse the bitmap image, to obtain parsed information, the parsed information being bitmap image encoded data; a querying unit 123, configured to query the pre-stored information corresponding to the mark; a second determining unit 124, configured to determine whether the parsed information conforms to the pre-stored information; and an extraction unit 125, configured to extract and output the pre-stored information in a case where the parsed information conforms to the pre-stored information.

The mark embedded inside the substrate, mainly comprises two types of information. One type of information is used for indicating identity of the substrate; and according to the information, it may be determined whether the substrate is a preset substrate which needs to be aligned and assembled, and the other type of information is used for indicating the position information of the substrate, for accurately cell-assembly according to the position information in the subsequent cell-assembly process.

Due to a possible error of the content of the mark or a non-mark part existing in the periphery of the mark, it is necessary to compare the parsed information, which is obtained through parsing the mark, with the pre-stored information; for example, corresponding pre-stored information can be queried in a data link table according to header information of the bitmap encoded data, and if the parsed information conforms to the pre-stored information (for example, conforms in format and/or content), it can be determined that the parsed information is accurate and valid, so that the pre-stored information can be output for use in the subsequent process.

The second optical transceiver unit 121 may be an infrared light source generating element, and the generated infrared light source may be emitted by an LED head. In addition, the second optical transceiver unit 121 can be configured to emit the light ray only when the substrate is determined to be valid by the detecting module; if the substrate is not determined to be valid but the second optical transceiver unit 121 is forced to emit the light ray, then the second optical transceiver unit 121 may send out an alarm and may further remove a process or program of parsing the bitmap image encoded data, so as to improve an anti-counterfeiting effect.

For example, the exemplary information extracting module 12 may further include: a filter unit 126, disposed between the second optical transceiver unit and the bitmap image, configured to filter out the projection of the non-mark part, and the projection is generated under the irradiation of the light ray emitted by the second optical transceiver unit 121.

Thus, the bitmap image corresponds to real information of the mark can be obtained, to avoid influence of the projection generated by a stain or a non-mark part in the bitmap image, and to further improve accurate extraction of information corresponding to the mark.

For example, the exemplary information extracting module may further include: an exposing unit 127, configured to expose the bitmap image, so that the gray-scale of the bitmap image corresponding to the mark is within a preset range of gray-scale, while the gray-scale of the bitmap image of the non-mark part is outside the preset range of gray-scale; for example, the second optical transceiver unit 121 is configured to obtain the bitmap image within the preset range of gray-scale.

For example, the gray-scale value obtained after exposure can be adjusted by adjusting time for exposure and a frame rate of pattern, and the gray-scale value of the bitmap image of a non-mark part or a stain after exposure is outside the preset range of gray-scale, which, thus, can ensure accuracy of the bitmap image obtained, and further ensure accurate extraction of the information corresponding to the mark.

For example, the extraction unit 125 is configured to extract the header information of the bitmap image encoded data, query the pre-stored information corresponding to the header information, determine whether the pre-stored information is identical to the data information in the image encoded data or not, and if yes, to extract and output the pre-stored information, and if no, to send prompt information or notice.

For example, the pre-stored information may be stored in a data link table. The outputting operation for the extracted pre-stored information may be performed in following ways for example:

If the file type corresponding to the pre-stored information is a text file, then the file can be displayed directly though a display screen;

If the file type corresponding to the pre-stored information is a picture file, then the file can be displayed directly though the display screen;

If the file type corresponding to the pre-stored information is a video file, then the file's image part can displayed directly though the display screen, and its sound part can played or outputted though a power amplifier speaker;

If the file type corresponding to the pre-stored information is an audio file, then the file can be played or outputted though the power amplifier speaker.

Figure 3:
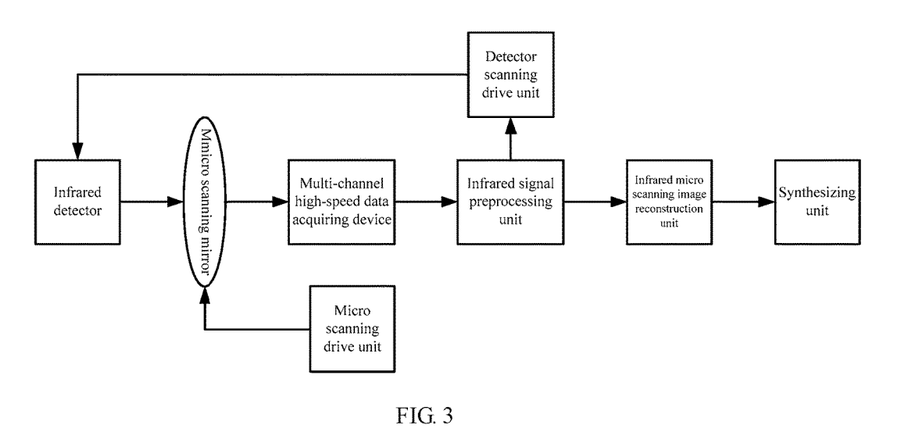
FIG. 3 shows a schematic diagram of signal flow according to an embodiment of the present disclosure.

As illustrated in FIG. 3, the first optical transceiver unit 111 and the second optical transceiver unit 121 in one example according to this embodiment may be combined into one element, namely, an infrared detector, which is provided with for example a micro scanning mirror, the micro scanning mirror works under the drive of a micro scanning drive unit, which can accurately scan the upper surface of the mark, so as to obtain the accurate depth at which the mark is embedded and the shape of the upper surface of the mark.

For example, a multi-channel high-speed data acquiring device can adopted to obtain the scan data of the infrared detector for each mark, and forward the scan data to an infrared signal preprocessing unit, for example the infrared signal preprocessing unit may comprise the filter unit 126 and/or the exposing unit 127, which is used for preprocessing a received infrared signal, so that the obtained bitmap image can correspond to the mark.

For example, an infrared scanning image reconstruction unit may process the preprocessed image to obtain a bitmap image, and further query the corresponding pre-stored information according to the bitmap image; then, a synthesizing unit performs a synthesizing process, for example, audio and image synthesis from the pre-stored information which conforms to the mark, and then output the synthesized result.

For example, the exemplary information extracting module 12 is further configured to parse a spare mark of the removed substrate to obtain spare information, query spare pre-stored information corresponding to the spare mark, and determine whether the spare information conforms to the spare pre-stored information or not, if yes, then extract the spare pre-stored information and output the spare pre-stored information.

A substrate under detection may be provided with a spare mark in addition to the mark intended for detection. Although the removed substrate is marked as invalid in the preceding process, or the parsed information corresponding to the mark does not conform to the pre-stored information, which means that the removed substrate is not applicable to be aligned and assembled with a pre-determined substrate, the removed substrate may still be applicable to be aligned and assembled with other kind of substrate, and thus, by parsing the spare mark, it may be determined whether the spare information conforms to the spare pre-stored information or not, if yes, it can be determined that the removed substrate can be aligned and assembled with the other kind of substrate according to the spare pre-stored information. Thereby, a utilization rate of the substrate is improved.

Figure 4:
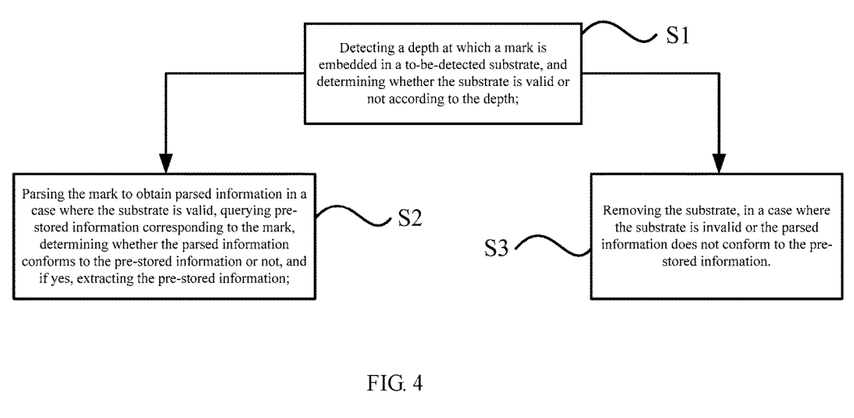
FIG. 4 shows a schematic flow chart of a substrate mark detection apparatus according to an embodiment of the present disclosure.

As illustrated in FIG. 4, a substrate mark detection method according to an embodiment of the present disclosure, comprises the following operations:

S1: detecting a depth at which a mark is embedded in a substrate to be detected, and determining whether the substrate is valid or not according to the depth at which the mark is embedded in the substrate;

S2: parsing the mark to obtain parsed information in a case where the substrate is valid, querying pre-stored information corresponding to the mark, determining whether the parsed information conforms to the pre-stored information or not, and if yes, to extract the pre-stored information and output the pre-stored information; and S3: removing the substrate in a case where the substrate is invalid or the parsed information does not conform to the pre-stored information.

Figure 5:
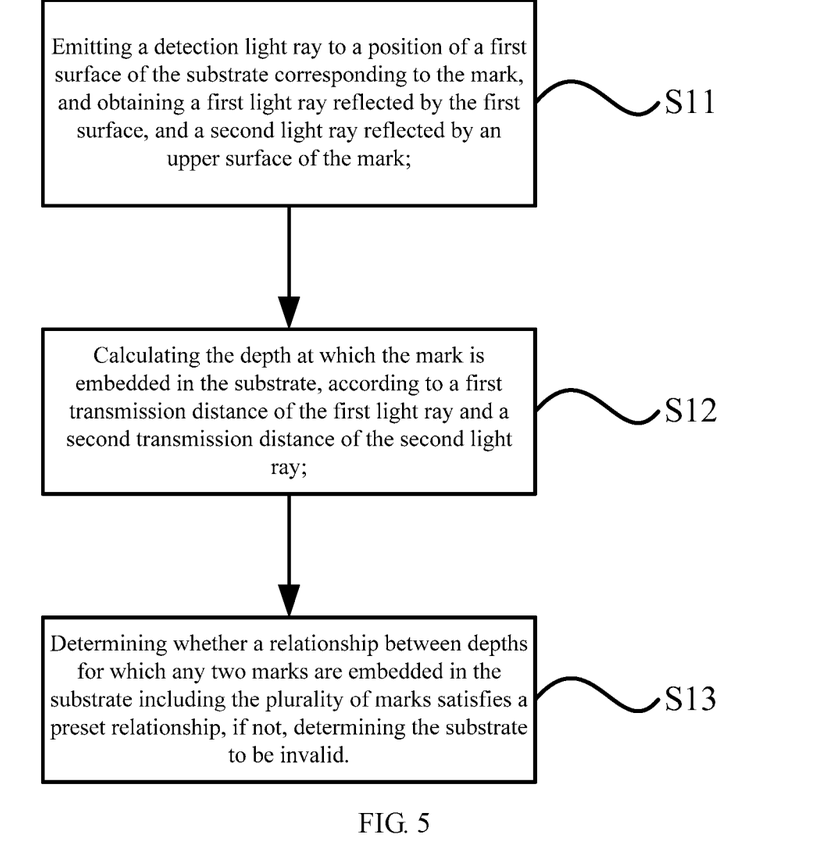
FIG. 5 shows a schematic flow chart of determining whether a substrate is valid or not according to an embodiment of the present disclosure.

As illustrated in FIG. 5, for example, the operation of detecting the depth at which a mark is embedded in a substrate to be detected and determining whether the substrate is valid or not according to the depth at which the mark is embedded in the substrate (i.e., step S1) may further include the following operations:

S11: emitting a detection light ray to a position of a first surface of the substrate corresponding to the mark, and obtaining a first light ray reflected by the first surface and a second light ray reflected by an upper surface of the mark;

S12: calculating the depth at which the mark is embedded in the substrate, according to a first transmission distance of the first light ray and a second transmission distance of the second light ray; and S13: determining whether a relationship between depths at which any two marks are embedded in the substrate including the plurality of marks satisfies a preset relationship or not, and if not, determine the substrate to be invalid.

Figure 6:
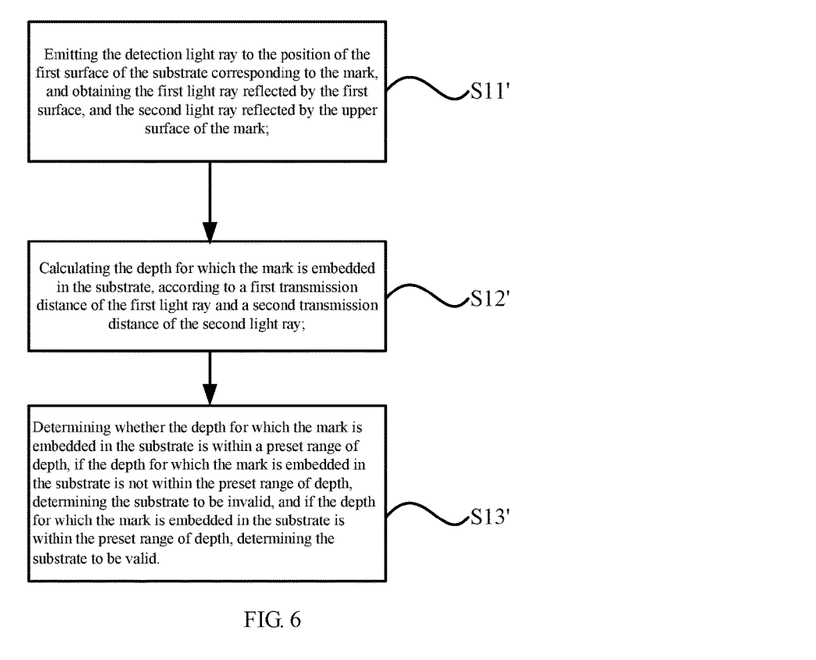
FIG. 6 shows a schematic flow chart of determining whether a substrate is valid or not according to another embodiment of the present disclosure.

As illustrated in FIG. 6, for example, the operation of detecting the depth at which a mark is embedded in a substrate to be detected and determining whether the substrate is valid or not according to the depth at which the mark is embedded in the substrate (i.e., step S1) may further include the following operations:\S11': emitting the detection light ray to the position of the first surface of the substrate corresponding to the mark, and obtaining the first light ray reflected by the first surface and the second light ray reflected by the upper surface of the mark;

S12': calculating the depth at which the mark is embedded in the substrate, according to the first transmission distance of the first light ray and the second transmission distance of the second light ray; and S13': determining whether the depth at which the mark is embedded in the substrate is within a preset range of depth, if the depth at which the mark is embedded in the substrate is not within the preset range of depth, determining the substrate to be invalid, and if the depth at which the mark is embedded in the substrate is within the preset range of depth, determining the substrate to be valid.

For example, in the case where the substrate includes a plurality of marks, and the first determining unit 113 is further configured to determine whether a depth for which each mark is embedded in the substrate is within the preset range of depth or not, if the depth for any one mark is embedded in the substrate is not within the preset range of depth, determine that the substrate is invalid, and if the depth for which each mark is embedded in the substrate is within the preset range of depth, then determine that the substrate is valid.

Figure 7:
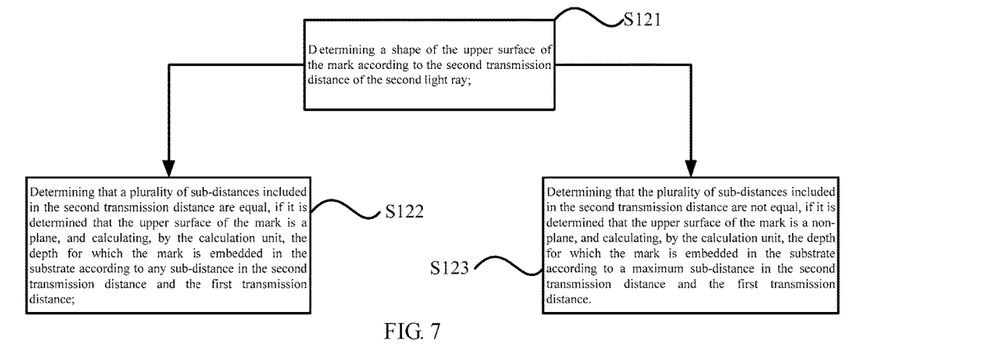
FIG. 7 shows a schematic flow chart of calculating a depth at which a mark is embedded in a substrate according to an embodiment of the present disclosure.

As illustrated in FIG. 7, for example, the operation of calculating the depth at which the mark is embedded in the substrate according to a first transmission distance of the first light ray and a second transmission distance of the second light ray (i.e., step S12) may further include the following operations:

S121: determining a shape of the upper surface of the mark according to the second transmission distance of the second light ray;

S122: determining that a plurality of sub-distances included in the second transmission distance are equal to each other, if it is determined that the upper surface of the mark is a plane, and calculating, by way of the calculation unit, the depth at which the mark is embedded in the substrate according to any sub-distance in the second transmission distance and the first transmission distance; and S123: determining that the plurality of sub-distances included in the second transmission distance are not equal to each other, if it is determined that the upper surface of the mark is not a plane, and calculating, by way of the calculation unit, the depth at which the mark is embedded in the substrate according to a maximum sub-distance in the second transmission distance and the first transmission distance.

Figure 8:
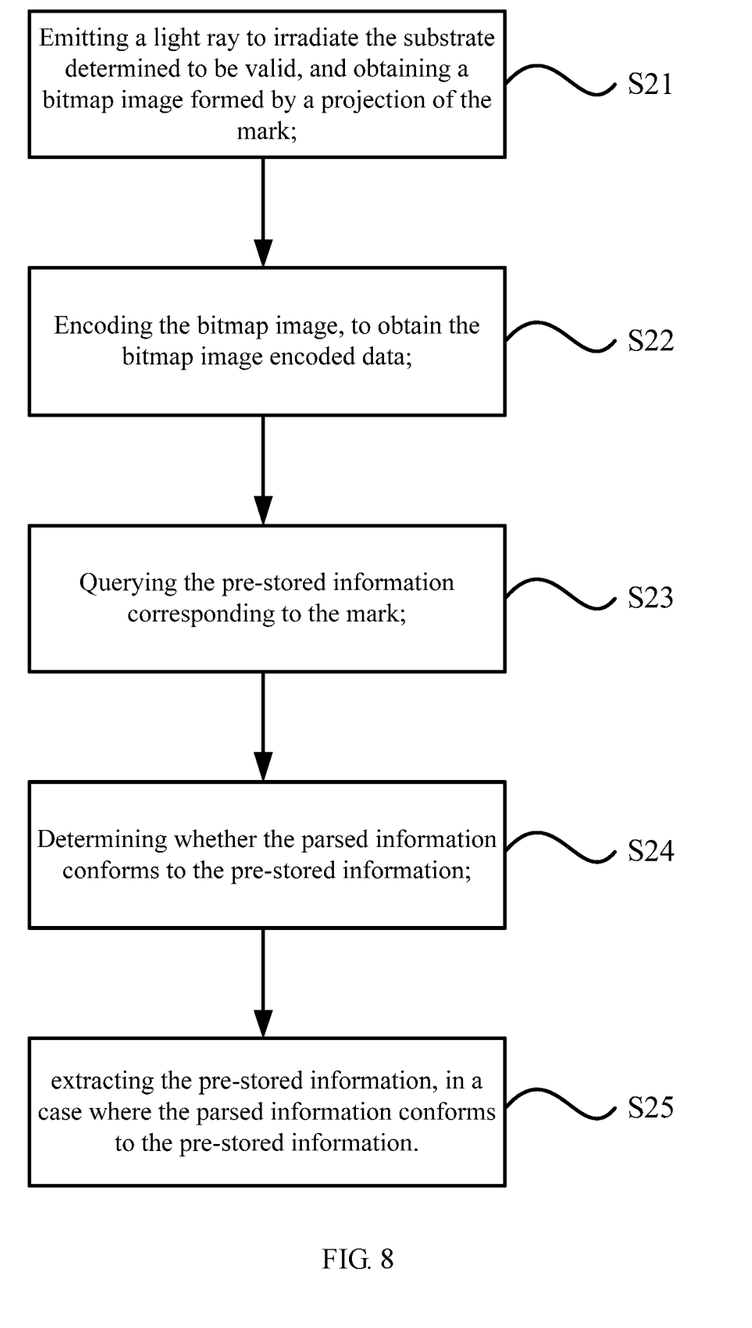
FIG. 8 shows a schematic flow chart of extracting information corresponding to each mark and outputting the same according to an embodiment of the present disclosure.

As illustrated in FIG. 8, for example, the operation of extracting the information corresponding to the mark and outputting the same (i.e., step S2) may further include the following operations:

S21: emitting a light ray to irradiate the substrate that is determined to be valid in the above step S1, and obtaining a bitmap image formed by a projection of the mark;

S22: parsing the bitmap image to obtain parsed information, the parsed information being bitmap image encoded data;

S23: querying the pre-stored information corresponding to the mark;

S24: determining whether the parsed information conforms to the pre-stored information; and S25: extracting the pre-stored information and outputting the pre-stored information, in a case where the parsed information conforms to the pre-stored information.

For example, the operation of obtaining a bitmap image formed by a projection of the mark (i.e., step S21) may further include: filtering out a projection of a non-mark part; the projection of the non-mark part is generated under irradiation of the light ray emitted by the second optical transceiver unit.

For example, the operation of obtaining a bitmap image formed by a projection of the mark (i.e., step S21) may further include: exposing the bitmap image, so that a gray-scale of the bitmap image corresponding to the mark is within a preset range of gray-scale and a gray-scale of the bitmap image of the non-mark is outside the preset range of gray-scale, and obtaining the bitmap image within the preset range of gray-scale.

For example, the operation of extracting the pre-stored information, according to the bitmap image encoded data and outputting the same (i.e., step S23) may further include: extracting header information of the bitmap image encoded data, querying the pre-stored information corresponding to the header information, determining whether the pre-stored information is identical to data information in the image encoded data or not, if yes, extracting the pre-stored information and output the pre-stored information, and if no, sending prompt information or notice.

For example, the operation may further include: parsing a spare mark of the removed substrate to obtain spare information, querying spare pre-stored information corresponding to the spare mark, and determining whether the spare information conforms to the spare pre-stored information or not, if yes, then extracting the spare pre-stored information and outputting the same.

One person of ordinary skill in the related art should understand that the embodiments of the present disclosure may be provided as a method, an apparatus (a device), or a computer program product. Accordingly, embodiments of the present disclosure can be implemented by a full hardware embodiment, a full software embodiment, or combination embodiments of software and hardware. Also, embodiments of the present disclosure can be implemented as a computer program product that is realized on one or more computer-usable storage media (including, but not limited to, magnetic disc memory, CD-ROM, optical memory, etc.) recording computer-usable program codes thereon.

The present disclosure is described herein with reference to flowcharts and/or block diagrams of methods, apparatuses (device), and computer program products according to the embodiments of the present disclosure. It should be understood that each flow and/or block in the flowchart and/or block diagram, and a combination of flows and/or blocks in the flowchart and/or block diagram can be implemented by computer program instructions. These computer program instructions may be provided to a general purpose computer, a special purpose computer, an embedded processor or a processor of other programmable data processing apparatus to form a machine, such that devices for implementing functions specified by one or more flows in a flowchart and/or one or more blocks in a block diagram may be generated by executing the instructions by the processor of the computer or other programmable data processing apparatus.

These computer program modules including instructions may further be stored in a computer-readable memory that can guide a computer or other programmable data processing apparatus to function in a particular manner, such that the instructions stored in the computer-readable memory produce a manufactured article including an instruction device, the instruction device implementing the functions specified by one or more flows in a flowchart and/or one or more blocks in a block diagram.

These computer program instructions may also be loaded to a computer or other programmable data processing apparatus, such that a series of process steps can be executed on the computer or other programmable data processing apparatus to produce process implemented by the computer, thereby, the instructions executed on the computer or other programmable data processing apparatus provide steps of the functions specified by one or more flows in a flowchart and/or one or more blocks in a block diagram.

For example, in the embodiment of the present disclosure, the substrate mark detection apparatus may comprise a processor, a memory, and computer program instructions stored in the memory; when the computer program instructions are executed by the processor, the processor can implement at least one specified function, for example, of the detecting module, the information extracting module, and the sorting module, and further, for example, may implement all or part of at least one specified function of the first optical transceiver unit, the calculation unit 112, the first determining unit 113, the second optical transceiver unit 121, the parsing unit 122, the querying unit 123, the second determining unit 124, the extraction unit 125, the filter unit 126, and the exposing unit 127 as described above. Furthermore, for example, the calculation unit 112, the first determining unit 113, the second optical transceiver unit 121, the parsing unit 122, the querying unit 123, the second determining unit 124, the extraction unit 125, the filter unit 126, and the exposing unit 127 can be implemented at least partially by way of hardware, firmware, or software.

For example, one embodiment of the present disclosure provides a substrate mark detection apparatus, comprising: a processor; a memory; and computer program instructions stored in the memory. For example, the computer program instructions are embodied in one or more modules. When the computer program instructions are run by the processor, the processor executes operations of: detecting a depth at which a mark is embedded in a substrate to be detected, and determining whether the substrate is valid or not according to the depth at which the mark is embedded in the substrate; parsing the mark to obtain parsed information in a case where the substrate is valid, querying pre-stored information corresponding to the mark, determining whether the parsed information conforms to the pre-stored information or not, and if yes, extracting the pre-stored information and outputting the pre-stored information; and removing the substrate, in a case where the substrate is invalid or the parsed information does not conform to the pre-stored information.

For example, the substrate mark detection apparatus may further comprise a first optical transceiver unit, configured to emit a detection light ray to a position of a first surface of the substrate corresponding to the mark.

For example, the substrate mark detection apparatus may further comprise a second optical transceiver unit, configured to emit a light ray to irradiate the substrate determined to be valid by the detecting module and obtain a bitmap image formed by a projection of the mark, for parsing the mark.

The foregoing illustrates the technical solutions of the present disclosure in detail in conjunction with the drawings, in consideration of inability to accurately detecting the mark in the substrate in a related art. The technical solutions according to the present disclosure, by detecting the mark in the substrate, determining according to the depth at which the mark is embedded in the substrate, can conveniently and accurately determine validity of the substrate, so as to avoid detection of the invalid substrate in the subsequent process, improve overall efficiency of detecting the substrate, and can only output the information of the mark in the valid substrate, to reduce work of processing useless information.

What are described above is related to the illustrative embodiments of the disclosure only and not limitative to the protecting scope of the present disclosure. The protecting scopes of the present disclosure are defined by the accompanying claims.

This application claims the benefit of priority from Chinese patent application No. 201510299662.8, filed on Jun. 3, 2015, the disclosure of which is incorporated herein in its entirety by reference as a part of the present application.

What is claimed is:

1. A substrate mark detection apparatus, comprising:
   a detecting module, configured to detect a depth at which a mark is embedded in a substrate to be detected and determine whether the substrate is valid or not according to the depth at which the mark is embedded in the substrate;
   an information extracting module, configured to parse the mark to obtain parsed information in a case where the substrate is valid, query pre-stored information corresponding to the mark, determine whether the parsed information conforms to the pre-stored information or not, and if yes, to extract the pre-stored information and output the pre-stored information; and a sorting module, configured to remove the substrate, in a case where the substrate is invalid or the parsed information does not conform to the pre-stored information.

2. The substrate mark detection apparatus according to claim 1, wherein, the detecting module includes:
   a first optical transceiver unit, configured to emit a detection light ray to a position of a first surface of the substrate corresponding to the mark, and receive a first light ray reflected by the first surface and a second light ray reflected by an upper surface of the mark;
   a calculation unit, configured to calculate the depth at which the mark is embedded in the substrate, according to a first transmission distance of the first light ray and a second transmission distance of the second light ray;
   a first determining unit, configured to determine whether a relationship between depths at which any two of the marks are embedded in the substrate including the plurality of marks satisfies a preset relationship, to determine whether the substrate is valid or not.

3. The substrate mark detection apparatus according to claim 1, wherein, the detecting module includes:
   a first optical transceiver unit, configured to emit a detection light ray to a position of a first surface of the substrate corresponding to the mark, and receive a first light ray reflected by the first surface and a second light ray reflected by an upper surface of the mark;
   a calculation unit, configured to calculate the depth at which the mark is embedded in the substrate, according to a first transmission distance of the first light ray and a second transmission distance of the second light ray; and
   a first determining unit, configured to determine whether the depth at which the mark is embedded in the substrate is within a preset range of depth, if the depth at which the mark is embedded in the substrate is not within the preset range of depth, determine that the substrate is invalid, and if the depth at which the mark is embedded in the substrate is within the preset range of depth, determine that the substrate is valid.

4. The substrate mark detection apparatus according to claim 3, wherein, the first determining unit is further configured to determine a shape of the upper surface of the mark according to the second transmission distance of the second light ray;
   if it is determined that the upper surface of the mark is a plane, then it is determined that a plurality of sub-distances included in the second transmission distance are equal, and the calculation unit is further configured to calculate the depth at which the mark is embedded in the substrate according to any sub-distance in the second transmission distance and the first transmission distance, and
   if it is determined that the upper surface of the mark is not a plane, then it is determined that the plurality of sub-distances included in the second transmission distance are not equal, and the calculation unit is further configured to calculate the depth at which the mark is embedded in the substrate according to a maximum sub-distance in the second transmission distance and the first transmission distance.

5. The substrate mark detection apparatus according to claim 1, wherein, the information extracting module includes:
   a second optical transceiver unit, configured to emit a light ray to irradiate the substrate determined to be valid by the detecting module, and obtain a bitmap image formed by a projection of the mark;
   a parsing unit, configured to parse the bitmap image to obtain parsed information, wherein the parsed information is bitmap image encoded data;
   a querying unit, configured to query the pre-stored information corresponding to the mark;
   a second determining unit, configured to determine whether the parsed information conforms to the pre-stored information; and
   an extraction unit, configured to extract and output the pre-stored information, in a case where the parsed information conforms to the pre-stored information.

6. The substrate mark detection apparatus according to claim 5, wherein, the information extracting module further includes:
   a filter unit, disposed between the second optical transceiver unit and the bitmap image, configured to filter out a projection of a non-mark part generated under irradiation of the light ray emitted by the second optical transceiver unit.

7. The substrate mark detection apparatus according to claim 5, wherein, the information extracting module further includes:
   an exposing unit, configured to expose the bitmap image, so that a gray-scale of the bitmap image corresponding to the mark is within a preset range of gray-scale and a gray-scale of the bitmap image of the non-mark is outside the preset range of gray-scale,
   wherein the second optical transceiver unit is further configured to obtain the bitmap image within the preset range of gray-scale.

8. The substrate mark detection apparatus according to claim 5, wherein, the extraction unit is further configured to extract the header information of the bitmap image encoded data, query the pre-stored information corresponding to the header information, determine whether the pre-stored information is identical to data information in the image encoded data or not, if yes, to extract and output the pre-stored information, and if no, send prompt information.

9. The substrate mark detection apparatus according to claim 1, wherein, the information extracting module is further configured to parse a spare mark of the substrate that is removed to obtain spare information, query spare pre-stored information corresponding to the spare mark, and determine whether the spare information conforms to the spare pre-stored information or not, if yes, then extract the spare pre-stored information and output the spare pre-stored information.

10. A substrate mark detection apparatus, comprising:
   a processor;
   a memory; and
   one or more modules stored in the memory and configured for execution by the processor, the one or more module comprising instructions for:
   detecting a depth at which a mark is embedded in a substrate to be detected, and determining whether the substrate is valid or not according to the depth at which the mark is embedded in the substrate;
   parsing the mark to obtain parsed information in a case where the substrate is valid, querying pre-stored information corresponding to the mark, determining whether the parsed information conforms to the pre-stored information or not, and if yes, to extract the pre-stored information and output the pre-stored information; and removing the substrate, in a case where the substrate is invalid or the parsed information does not conform to the pre-stored information.

11. A substrate mark detection method, comprising:
   detecting a depth at which a mark is embedded in a substrate to be detected, and determining whether the substrate is valid or not according to the depth at which the mark is embedded in the substrate;
   parsing the mark to obtain parsed information in a case where the substrate is valid, querying pre-stored information corresponding to the mark, determining whether the parsed information conforms to the pre-stored information or not, and if yes, to extract the pre-stored information and output the pre-stored information; and
   removing the substrate, in a case where the substrate is invalid or the parsed information does not conform to the pre-stored information.

12. The substrate mark detection method according to claim 11, wherein, the operation of detecting a depth at which a mark is embedded in a substrate to be detected and determining whether the substrate is valid or not according to the depth at which the mark is embedded in the substrate includes:
   emitting a detection light ray to a position of a first surface of the substrate corresponding to the mark, and obtaining a first light ray reflected by the first surface and a second light ray reflected by an upper surface of the mark;
   calculating the depth at which the mark is embedded in the substrate, according to a first transmission distance of the first light ray and a second transmission distance of the second light ray; and
   determining whether a relationship between depths at which any two marks are embedded in the substrate including the plurality of marks satisfies a preset relationship or not, and if not, determining the substrate to be invalid.

13. The substrate mark detection method according to claim 11, wherein, the operation of detecting a depth at which a mark is embedded in a substrate to be detected and determining whether the substrate is valid or not according to the depth at which the mark is embedded in the substrate includes:
   emitting a detection light ray to a position of a first surface of the substrate corresponding to the mark, and obtaining a first light ray reflected by the first surface and a second light ray reflected by an upper surface of the mark;
   calculating the depth at which the mark is embedded in the substrate, according to a first transmission distance of the first light ray and a second transmission distance of the second light ray; and
   determining whether the depth at which the mark is embedded in the substrate is within a preset range of depth, if the depth at which the mark is embedded in the substrate is not within the preset range of depth, determining the substrate to be invalid, and if the depth at which the mark is embedded in the substrate is within the preset range of depth, determining the substrate to be valid.

14. The substrate mark detection method according to claim 13, wherein, the substrate includes a plurality of marks, if the depth for which any one mark is embedded in the substrate is not within the preset range of depth, it is determined that the substrate is invalid; and if the depth for which each mark is embedded in the substrate is within the preset range of depth, then it is determined that the substrate is valid.

15. The substrate mark detection method according to claim 13, wherein, the operation of calculating the depth at which the mark is embedded in the substrate according to a first transmission distance of the first light ray and a second transmission distance of the second light ray includes:
   determining a shape of the upper surface of the mark according to the second transmission distance of the second light ray;
   determining that a plurality of sub-distances included in the second transmission distance are equal if it is determined that the upper surface of the mark is a plane, and calculating the depth at which the mark is embedded in the substrate according to any sub-distance in the second transmission distance and the first transmission distance; and
   determining that the plurality of sub-distances included in the second transmission distance are not equal if it is determined that the upper surface of the mark is not a plane, and calculating the depth at which the mark is embedded in the substrate according to a maximum sub-distance in the second transmission distance and the first transmission distance.

16. The substrate mark detection method according to claim 11, wherein, the operation of extracting the information corresponding to the mark and outputting the same includes:
   emitting a light ray to irradiate the substrate determined to be valid in detection, and obtaining a bitmap image formed by a projection of the mark;
   parsing the bitmap image to obtain parsed information, the parsed information being bitmap image encoded data;
   querying the pre-stored information corresponding to the mark;
   determining whether the parsed information conforms to the pre-stored information; and
   extracting the pre-stored information and outputting the pre-stored information in a case where the parsed information conforms to the pre-stored information.

17. The substrate mark detection method according to claim 16, wherein, the operation of obtaining a bitmap image formed by a projection of the mark includes:
   filtering out a projection of a non-mark part generated under irradiation of the light ray emitted by the second optical transceiver unit.

18. The substrate mark detection method according to claim 16, wherein, the operation of obtaining a bitmap image formed by a projection of the mark includes:
   exposing the bitmap image, so that a gray-scale of the bitmap image corresponding to the mark is within a preset range of gray-scale and a gray-scale of the bitmap image of the non-mark is outside the preset range of gray-scale, and obtaining the bitmap image within the preset range of gray-scale.

19. The substrate mark detection method according to claim 16, wherein, the operation of extracting the corresponding information, according to the bitmap image encoded data, and outputting the same includes:
   extracting header information of the bitmap image encoded data, querying the pre-stored information corresponding to the header information, determining whether the pre-stored information is identical to data information in the image encoded data or not, if yes, to extract the pre-stored information and output the pre-stored information, and if no, to send prompt information.

20. The substrate mark detection method according to claim 11, further comprising:

parsing a spare mark of the substrate that is removed to obtain spare information, querying spare pre-stored information corresponding to the spare mark, and determining whether the spare information conforms to the spare pre-stored information or not, and if yes, then extracting the spare pre-stored information and outputting the same.

* * * * *